United States Patent
Wu

(10) Patent No.: US 9,844,422 B1
(45) Date of Patent: Dec. 19, 2017

(54) DENTAL BRACKET

(71) Applicant: Chuan-Chung Wu, Taichung (TW)

(72) Inventor: Chuan-Chung Wu, Taichung (TW)

( * ) Notice: Subject to any disclaimer, the term of this patent is extended or adjusted under 35 U.S.C. 154(b) by 1 day.

(21) Appl. No.: 15/218,865

(22) Filed: Jul. 25, 2016

(51) Int. Cl.
*A61C 3/00* (2006.01)
*A61C 7/12* (2006.01)
*A61C 7/28* (2006.01)
*A44C 15/00* (2006.01)

(52) U.S. Cl.
CPC ............ *A61C 7/125* (2013.01); *A44C 15/007* (2013.01); *A61C 7/287* (2013.01)

(58) Field of Classification Search
CPC .............................................. A61C 7/28–7/34
USPC ...................................................... 433/8–24
See application file for complete search history.

(56) References Cited

U.S. PATENT DOCUMENTS

| | | | | |
|---|---|---|---|---|
| 4,279,593 A * | 7/1981 | Rohlcke | A61C 7/12 433/8 |
| 4,355,975 A * | 10/1982 | Fujita | A61C 7/143 433/11 |
| 4,687,441 A * | 8/1987 | Klepacki | A61C 7/125 433/8 |
| 4,913,654 A * | 4/1990 | Morgan | A61C 7/125 433/11 |
| 5,356,288 A * | 10/1994 | Cohen | A61C 7/14 433/10 |
| 7,134,873 B2 * | 11/2006 | Miyaji | A61C 7/28 433/10 |
| 8,714,973 B2 * | 5/2014 | Zucchi | A61C 7/143 433/11 |
| 2005/0255422 A1 * | 11/2005 | Cordato | A61C 7/14 433/10 |
| 2006/0172248 A1 * | 8/2006 | Sernetz | A61C 7/282 433/8 |
| 2006/0228663 A1 * | 10/2006 | Darling | A61C 7/303 433/11 |
| 2006/0257808 A1 * | 11/2006 | Feller | A61C 7/00 433/2 |
| 2006/0292517 A1 * | 12/2006 | Smith | A61C 7/00 433/13 |
| 2007/0099145 A1 * | 5/2007 | Abels | A61C 7/14 433/10 |
| 2007/0269764 A1 * | 11/2007 | Feller | A61C 7/00 433/22 |
| 2008/0057459 A1 * | 3/2008 | Abels | A61C 7/125 433/10 |

(Continued)

*Primary Examiner* — Matthew Nelson
(74) *Attorney, Agent, or Firm* — WPAT, P.C., Intellectual Property Attorneys; Anthony King

(57) ABSTRACT

A dental bracket has a base and an engaging unit. The base has two engaged protrusions and two limiting protrusions. The engaging unit is mounted on the base and forms a space between the base and the engaging unit. The engaging unit has a plate, two engaging arms, and a blocking protrusion. The plate has a first surface and a second surface being flat and opposite the first surface. The two engaging arms are formed on the first surface of the plate and respectively engaged with the two engaged protrusions of the base. The blocking protrusion is formed on the first surface of the plate, is arranged between the two limiting protrusions of the base, and divides the space into two channels for inserting an archwire. The second surface of the engaging unit is flat and is able to decrease the foreign body sensation in the mouth.

9 Claims, 6 Drawing Sheets

(56) References Cited

U.S. PATENT DOCUMENTS

| | | | |
|---|---|---|---|
| 2010/0081106 A1* | 4/2010 | Park | A61C 7/12 433/8 |
| 2010/0129765 A1* | 5/2010 | Mohr | A61C 7/12 433/10 |
| 2011/0136071 A1* | 6/2011 | Levens | A61C 7/125 433/13 |
| 2012/0058443 A1* | 3/2012 | Tamura | A61C 7/287 433/13 |
| 2012/0156632 A1* | 6/2012 | Schiller | A61C 19/063 433/10 |
| 2013/0130189 A1* | 5/2013 | Roncone | A61C 7/30 433/11 |
| 2014/0038121 A1* | 2/2014 | Smith | A61C 7/282 433/17 |
| 2016/0367340 A1* | 12/2016 | Ward | A61C 7/287 |
| 2017/0156822 A1* | 6/2017 | Yu | A61C 7/143 |

* cited by examiner

US 9,844,422 B1

DENTAL BRACKET

BACKGROUND OF THE INVENTION

1. Field of the Invention

The present invention relates to an apparatus for orthodontics, and more particularly to a dental bracket with a smooth structure that can reduce the chance of tooth decay and the foreign body sensation in the mouth.

2. Description of Related Art

The malposition of teeth, also known as dental deviation, is often caused by excessive or inadequate space for teeth growth. The malposition of teeth not only diminishes the aesthetic appeal in the look of the patient, but also causes malocclusion and brings forth a negative effect on chewing.

There are many types of dental brackets used to correct the malposition of teeth. The traditional orthodontics bracket has a bracket body, an archwire, and an elastomeric ligature. The bracket body is glued on a tooth. The archwire is assembled into the bracket body. The elastomeric ligature is mounted on and around the bracket body to fix the archwire. The interaction between the bracket body and the archwire guides the tooth into a desired orientation. However, the elastomeric ligature is difficult to be mounted on and around the bracket body in the oral cavity. The orthodontics specialists require finer techniques to assemble the traditional orthodontics bracket.

A conventional self-ligating brace is provided for mitigate the defect of the traditional orthodontics bracket. The self-ligating brace has a brace body with an uneven outline and an archwire assembled into the brace body. The conventional self-ligating brace omits the elastomeric ligature and fixes the archwire by the brace body. Although the conventional self-ligating brace is easier than the traditional orthodontics bracket in assembly, the uneven outline of the brace body makes food debris easily stuck to the brace body, causes the brace body hard to be cleaned, and raises the chance of tooth decay. And more particularly, the uneven outline of the brace body continually rubs the interior of the mouth and causes a foreign body sensation in the mouth.

To overcome the shortcomings of the conventional self-ligating brace, the present invention provides a dental bracket to mitigate or obviate the aforementioned problems.

SUMMARY OF THE INVENTION

The main objective of the present invention is to provide a dental bracket that can reduce the chance of tooth decay and the foreign body sensation in the mouth.

The dental bracket comprises a base and an engaging unit. The base has two engaged protrusions and two limiting protrusions. The engaging unit is mounted on the base and forms a space between the base and the engaging unit. The engaging unit has a plate, two engaging arms, and a blocking protrusion. The plate has a first surface and a second surface being flat and opposite the first surface. The two engaging arms are formed on the first surface of the plate and respectively engaged with the two engaged protrusions of the base. The blocking protrusion is formed on the first surface of the plate, is arranged between the two limiting protrusions of the base, and divides the space into two channels for inserting an archwire. The second surface of the engaging unit is flat and is able to decrease the foreign body sensation in the mouth.

Other objects, advantages, and novel features of the invention will become more apparent from the following detailed description when taken in conjunction with the accompanying drawings.

DETAILED DESCRIPTION OF PREFERRED EMBODIMENT

Figure 1:
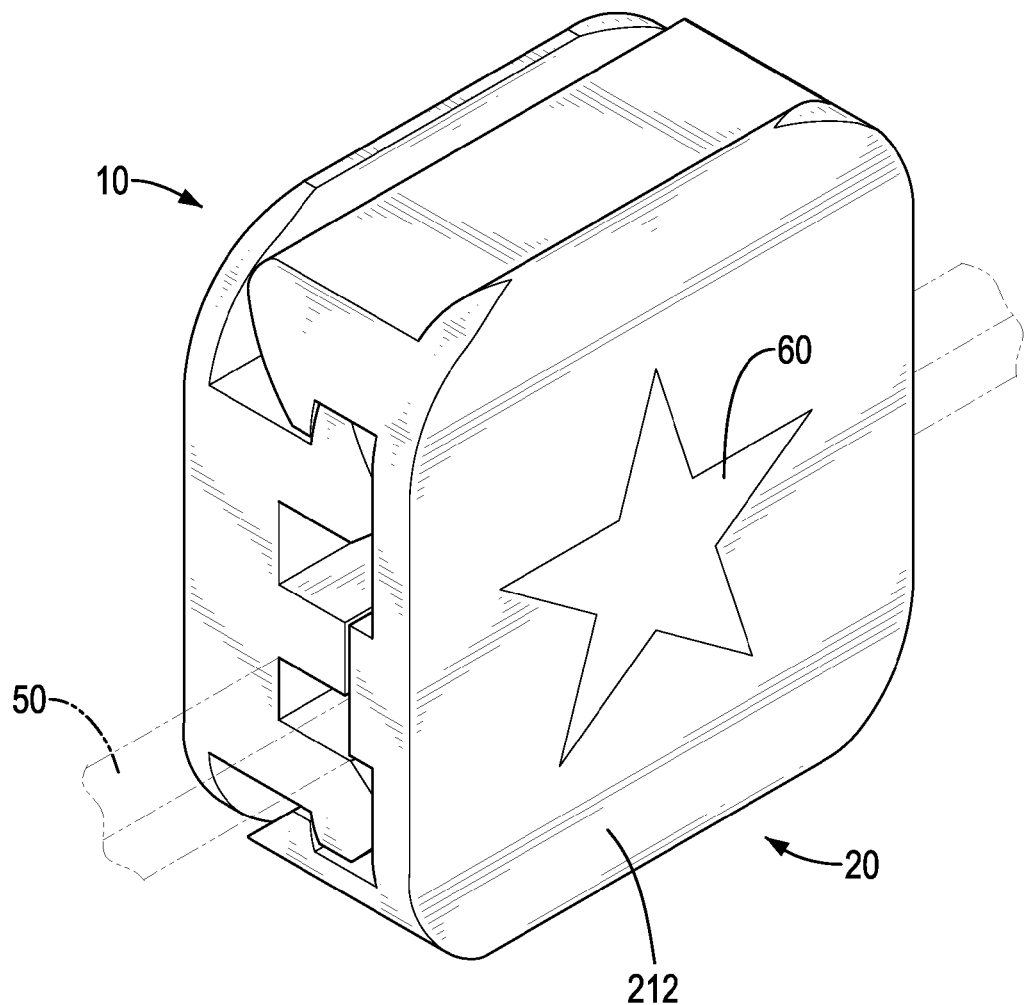
FIG. 1 is a perspective view of a dental bracket in accordance with the present invention.
Figure 2:
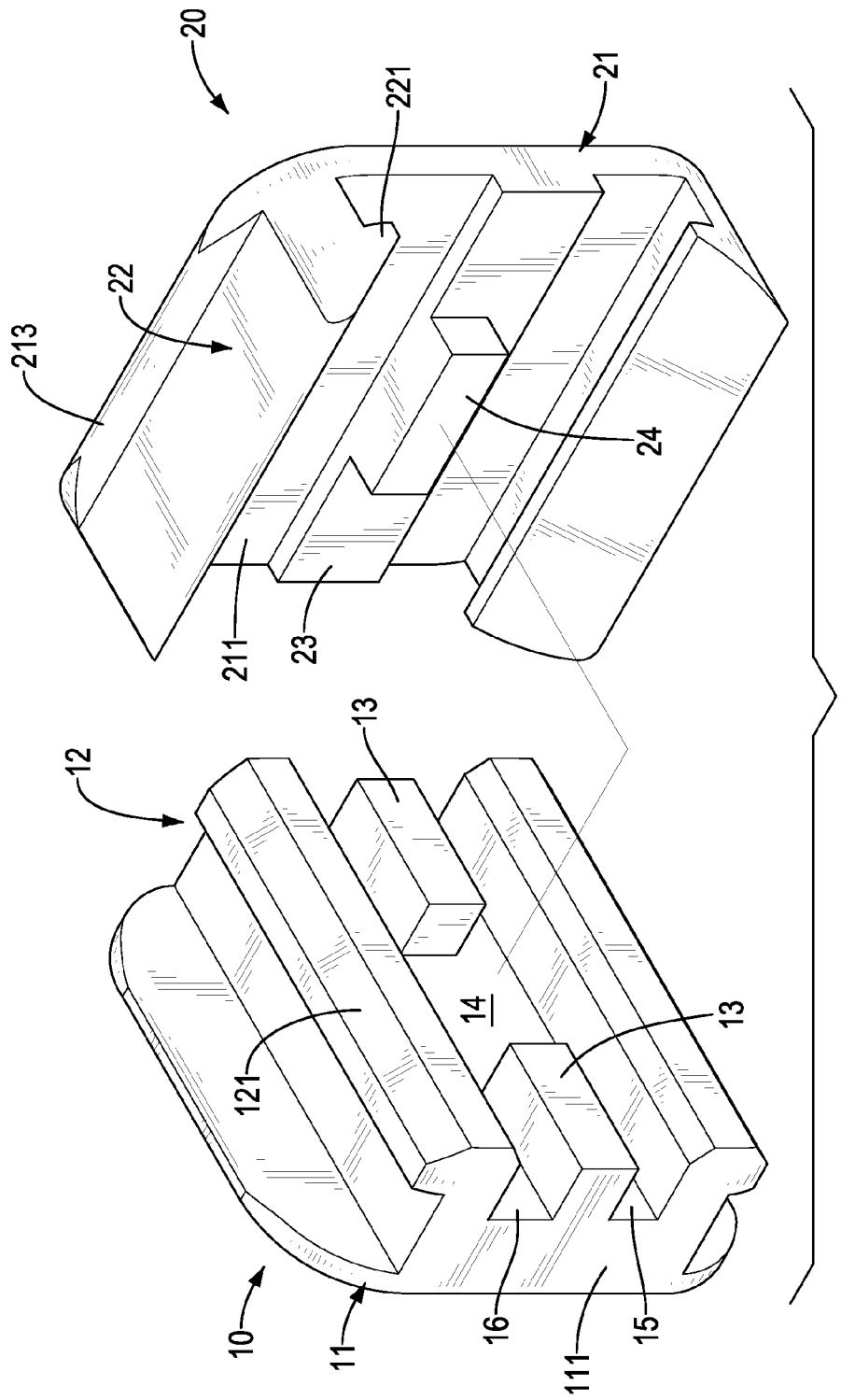
FIG. 2 is an exploded perspective view of the dental bracket in FIG. 1.

With reference to FIGS. 1 and 2, a dental bracket in accordance with the present invention comprises a base 10 and an engaging unit 20. The engaging unit 20 is mounted on the base 10.

Figure 3:
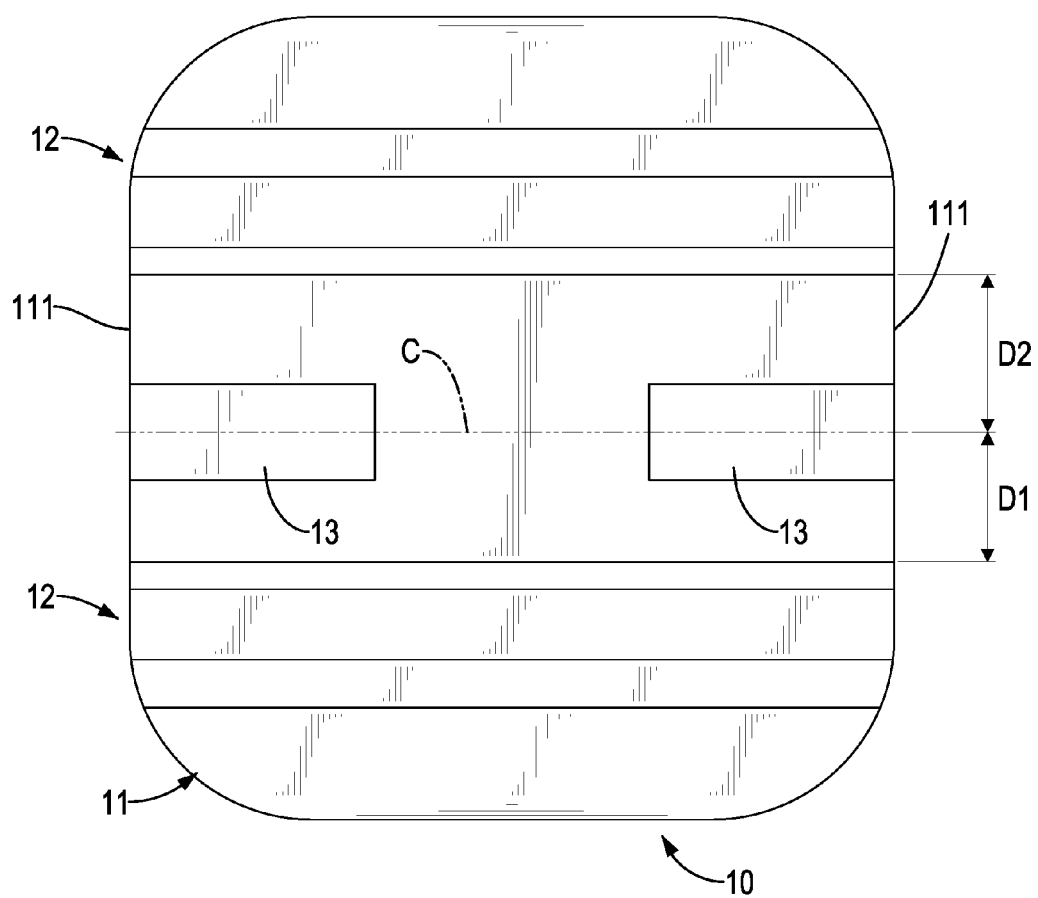
FIG. 3 is a front view of a base of the dental bracket in FIG. 1.

With reference to FIGS. 2 and 3, the base 10 has a longitudinal direction, a basal plate 11, two engaged protrusions 12, two limiting protrusions 13, and a gap 14. The basal plate 11 is rectangular and has a surface and two ends 111. The two ends 111 of the basal plate 11 are opposite each other in the longitudinal direction of the base 10. The two engaged protrusions 12 are spaced from each other, are formed on the surface of the basal plate 11, and extend along the longitudinal direction of the base 10. Each engaged protrusion 12 has a hook portion 121 distal from the basal plate 11. The two hook portions 121 of the two engaged protrusions 12 respectively face to two opposite directions. The two limiting protrusions 13 are spaced from each other, are arranged between the two engaged protrusions 12, extend along a longitudinal line C, and are formed on the surface of the basal plate 11. The longitudinal line C is spaced from the two engaged protrusions 12 respectively by a first distance D1 and a second distance D2. The first distance D1 is smaller than the second distance D2. The gap 14 is formed between the two limiting protrusions 13.

Figure 4:
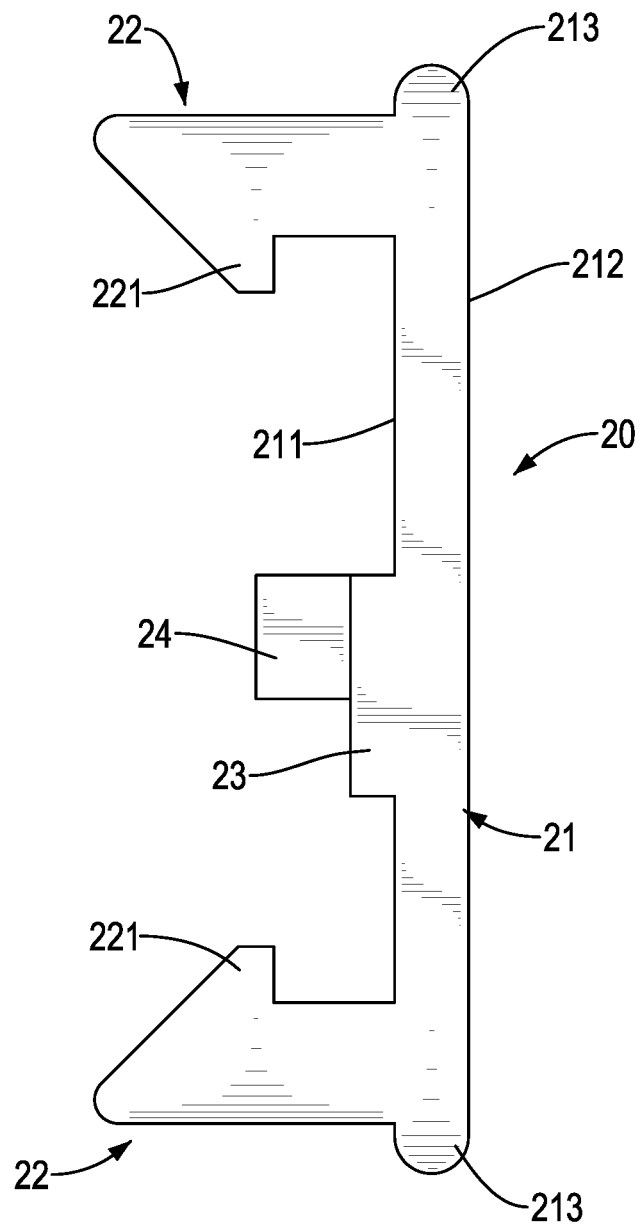
FIG. 4 is a side view of an engaging unit of the dental bracket in FIG. 1.

With reference to FIGS. 1, 2, and 4, the engaging unit 20 is mounted on the base 10 and forms a space between the base 10 and the engaging unit 20. The engaging unit 20 has a plate 21, two engaging arms 22, a pressing protrusion 23, and a blocking protrusion 24. The plate 21 has a longitudinal direction, a first surface 211, a second surface 212, two opposite sides 213, and two opposite ends. The second surface 212 is flat and is opposite the first surface 211 of the plate 21. The two opposite sides 213 extend along the longitudinal direction of the base 10, and each side 213 has a smooth side face. The two opposite ends of the plate 21 are opposite in the longitudinal direction of the plate 21. The two engaging arms 22 are spaced from each other, are formed on the first surface 211 of the plate 21, extend along the longitudinal direction of the base 10, and are respectively engaged with the two engaged protrusions 12 of the base 10. Each engaging arm 22 has a hook section 221 distal from the plate 21. The two hook sections 221 of the two engaging arms 22 face each other. The two engaging arms 22 are respectively engaged with the two engaged protrusions 12 by the two hook sections 221 and the two hook portions 121. The pressing protrusion 23 is formed on the first surface 211 of the plate 21, is arranged between the two engaging arms 22, extends along the longitudinal direction of the base 10 to the two opposite ends of the plate 21, and has an upper surface. The blocking protrusion 24 is formed on the upper surface of the pressing protrusion 23 and is arranged between the two limiting protrusions 13 of the base 10. The two limiting protrusions 13 and the blocking protrusion 24 divide the space between the base 10 and the engaging unit 20 into two channels extending along the longitudinal direction of the base 10.

Figure 5:
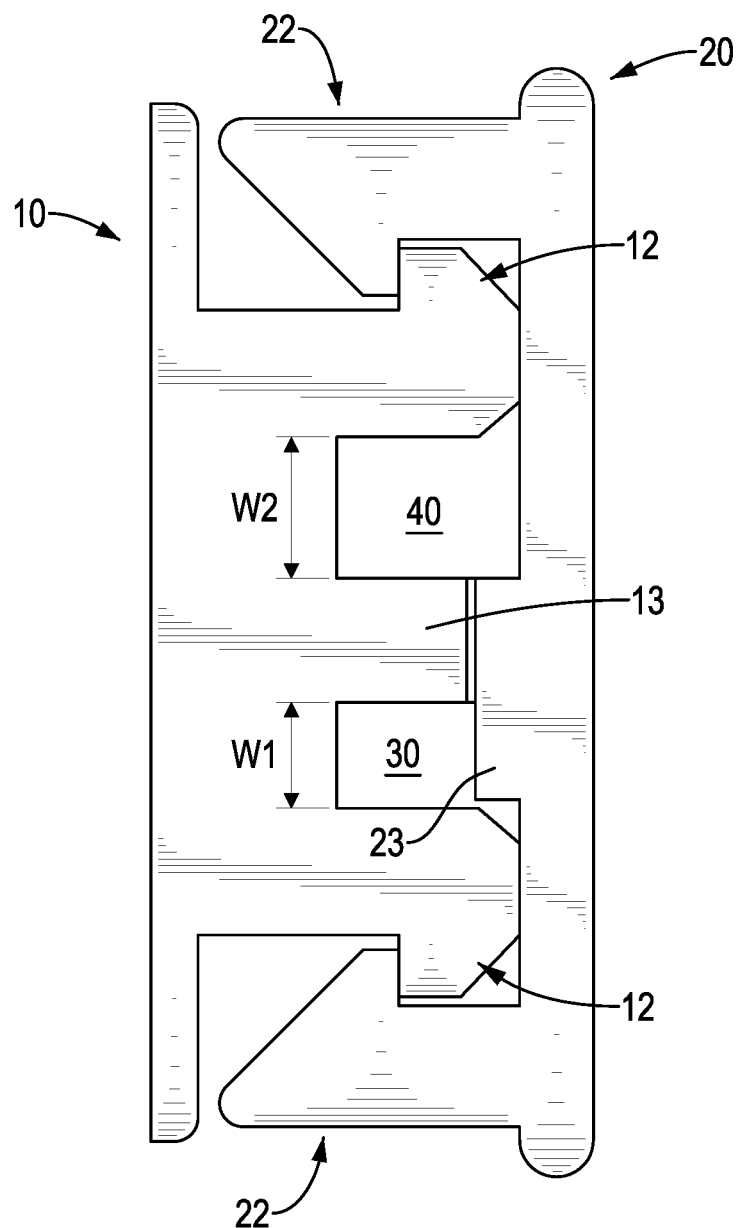
FIG. 5 is an operational side view of the dental bracket in FIG. 1.
Figure 6:
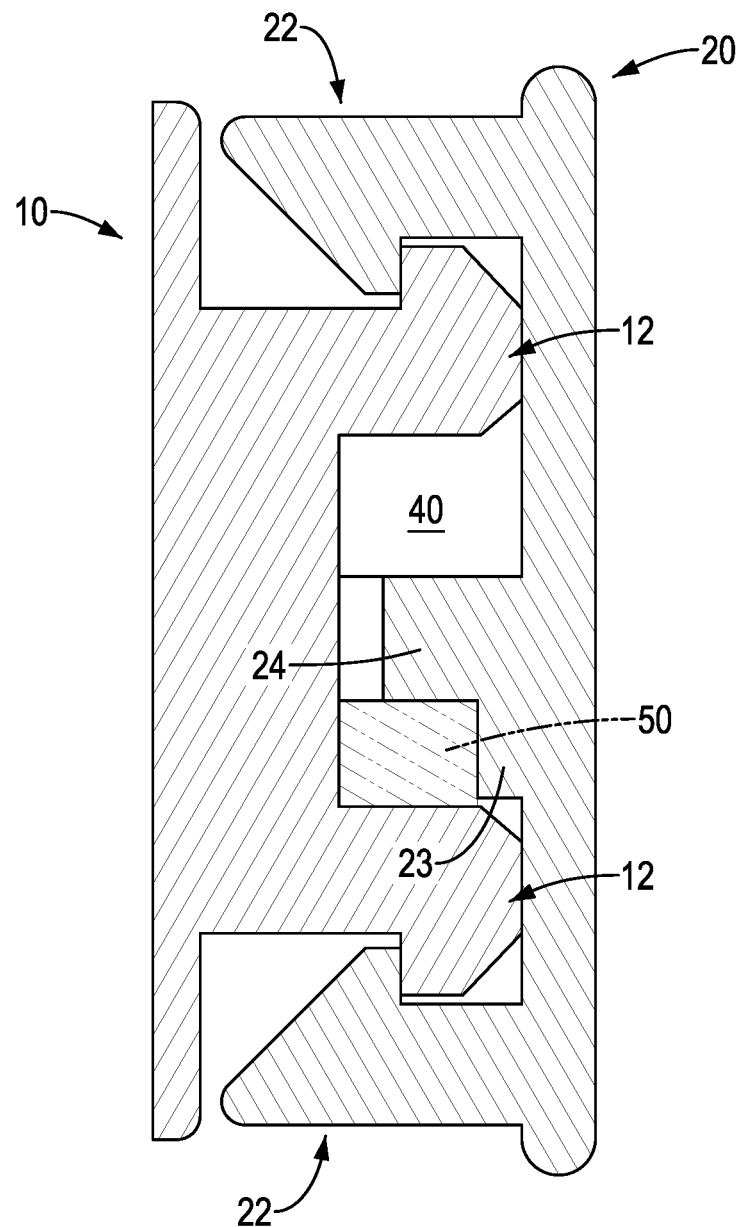
FIG. 6 is an operational cross-sectional side view of the dental bracket with an archwire in FIG. 1.

The pressing protrusion 23 and the blocking protrusion 24 may be independently formed on the first surface 211 of the plate 21, and the pressing protrusion 23 may be arranged between the blocking protrusion 24 and one of the two engaging arms 22. With reference to FIGS. 5 and 6, the two limiting protrusions 13 and the blocking protrusion 24 distinguish the two channels into a first channel 30 and a second channel 40. The first channel 30 and the second channel 40 respectively have a first width W1 and a second width W2. The first width W1 of the first channel 30 is smaller than the second width W2 of the second channel 40. The pressing protrusion 23 protrudes into the first channel 30.

With reference to FIGS. 1 and 5, an archwire 50 generally made of stainless steel can be optionally assembled into one of the first channel 30 and the second channel 40. As the archwire 50 is being assembled into the first channel 30, the pressing protrusion 23 presses the archwire 50 to prevent the archwire 50 and the dental bracket from sliding relative to each other. When the archwire 50 is assembled into the second channel 40 with the larger width W2, the archwire 50 and the dental bracket can slide relative to each other.

With reference to FIGS. 1 and 3, the flat second surface 212 of the plate 21 of the engaging unit 20 is hardly stuck with food debris and is able to reduce the chance of tooth decay. The flat second surface 212 of the plate 21 is also not easy to irritate the inner tissue of the mouth, reduces the rub occurring between the dental bracket and the inner tissue of the mouth, and decreases the foreign body sensation in the mouth. Furthermore, the flat second surface 212 of the plate 21 can be patterned with illustrations 60 to increase the visual appeal of the dental bracket. The two opposite sides 213 of the plate 21 of the engaging unit 20 with the smooth side faces can decrease the foreign body sensation in the mouth as well.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A dental bracket comprising:
   a base having
      a longitudinal direction;
      a basal plate having
         a surface;
         two ends opposite each other in the longitudinal direction of the base;
      two engaged protrusions spaced from each other, formed on the surface of the basal plate, and extending along the longitudinal direction of the base;
      two limiting protrusions spaced from each other, arranged between the two engaged protrusions, extending along a longitudinal line, and formed on the surface of the basal plate;
      a gap formed between the two limiting protrusions; and
   an engaging unit mounted on the base, forming a space between the base and the engaging unit, and having
      a plate having
         a first surface; and
         a second surface being flat and opposite the first surface of the plate;
      two engaging arms spaced from each other, formed on the first surface of the plate, extending along the longitudinal direction of the base, and respectively engaged with the two engaged protrusions; and
      a blocking protrusion formed on the first surface of the plate, arranged between the two limiting protrusions, and the blocking protrusion and the two limiting protrusions dividing the space into two channels extending along the longitudinal direction of the base.

2. The dental bracket as claimed in claim 1, wherein the engaging unit has a pressing protrusion formed on the first surface of the plate, arranged between the blocking protrusion and one of the two engaging arms, and protrudes into one of the two channels.

3. The dental bracket as claimed in claim 2, wherein the plate of the engaging unit has two opposite sides extending along the longitudinal direction of the base; and each side has a smooth side face.

4. The dental bracket as claimed in claim 3, wherein
   the longitudinal line along which the two limiting protrusions extend is spaced from the two engaged protrusions respectively by a first distance and a second distance being larger than the first distance;
   the two limiting protrusions and the blocking protrusion distinguish the two channels into a first channel and a second channel wider than the first channel; and
   the pressing protrusion protrudes into the first channel.

5. The dental bracket as claimed in claim 4, wherein the second surface is patterned with illustrations.

6. The dental bracket as claimed in claim 5, wherein
   each engaged protrusion has a hook portion being distal from the basal plate, and the two hook portions of the two engaged protrusions respectively face to two opposite directions;
   each engaging arm has a hook section being distal from the plate, and the two hook sections of the two engaging arms face each other;
   the two engaged protrusions and the two engaging arms are respectively engaged with each other by the two hook portions and the two hook sections.

7. The dental bracket as claimed in claim 3, wherein
   each engaged protrusion has a hook portion being distal from the basal plate, and the two hook portions of the two engaged protrusions respectively face to two opposite directions;
   each engaging arm has a hook section being distal from the plate, and the two hook sections of the two engaging arms face each other;
   the two engaged protrusions and the two engaging arms are respectively engaged with each other by the two hook portions and the two hook sections.

8. The dental bracket as claimed in claim 1, wherein the plate of the engaging unit has two opposite sides extending along the longitudinal direction of the base; and each side has a smooth side face.

9. The dental bracket as claimed in claim 1, wherein
the longitudinal line along which the two limiting protrusions extend is spaced from the two engaged protrusions respectively by a first distance and a second distance being larger than the first distance; and
the two limiting protrusions and the blocking protrusion distinguish the two channels into a first channel and a second channel wider than the first channel.

\* \* \* \* \*